(12) United States Patent
Seidel

(10) Patent No.: US 7,997,079 B2
(45) Date of Patent: Aug. 16, 2011

(54) SELF-REGULATED THERMAL ENERGY SYSTEM

(76) Inventor: Pessach Seidel, Motza Ilit (IL)

( * ) Notice: Subject to any disclaimer, the term of this patent is extended or adjusted under 35 U.S.C. 154(b) by 940 days.

(21) Appl. No.: 11/510,876

(22) Filed: Jul. 18, 2006

(65) Prior Publication Data

US 2007/0227146 A1  Oct. 4, 2007

Related U.S. Application Data

(63) Continuation-in-part of application No. PCT/IL2004/000360, filed on Apr. 29, 2004.

(30) Foreign Application Priority Data

Apr. 29, 2003  (IL) .......................................... 155665

(51) Int. Cl.
*F01K 13/00* (2006.01)
*F01K 1/00* (2006.01)
*F01K 3/00* (2006.01)

(52) U.S. Cl. .......................................... 60/659; 60/645

(58) Field of Classification Search .................. 60/645, 60/641.8, 641.13, 659; 126/640, 643, 437; 137/255, 468, 625.28; 165/104.19, 236, 165/253, 287, 288, 292, 293, 294, 296, 299, 165/300
See application file for complete search history.

(56) References Cited

U.S. PATENT DOCUMENTS

| | | | | |
|---|---|---|---|---|
| 3,977,197 A * | 8/1976 | Brantley, Jr. | | 60/659 |
| 4,129,177 A | 12/1978 | Adcock | | |
| 4,192,144 A * | 3/1980 | Pierce | | 60/641.8 |
| 4,287,942 A * | 9/1981 | Whitman | | 165/10 |
| 4,304,219 A * | 12/1981 | Currie | | 126/587 |
| 4,339,930 A * | 7/1982 | Kirts | | 62/235.1 |
| 4,357,932 A | 11/1982 | Stacy | | |
| 4,362,149 A * | 12/1982 | Thomson | | 126/400 |
| 4,373,573 A | 2/1983 | Madwed | | |
| 4,418,683 A * | 12/1983 | Friefeld et al. | | 126/400 |
| 4,523,629 A * | 6/1985 | Copeland | | 165/104.19 |
| 5,558,055 A * | 9/1996 | Schatz | | 123/142.5 R |
| 5,680,898 A * | 10/1997 | Rafalovich et al. | | 165/236 |
| 6,467,292 B1 * | 10/2002 | Praxmarer et al. | | 62/228.4 |

OTHER PUBLICATIONS

International Search Report published Mar. 31, 2005 for PCT/IL04/00360 filed Apr. 29, 2004.
Written Opinion of the International Searching Authority published Oct. 29, 2005 for PCT/IL04/00360 filed Apr. 29, 2004.
International Preliminary Report on Patentability published Nov. 4, 2005 for PCT/IL04/00360 filed Apr. 29, 2004.

* cited by examiner

*Primary Examiner* — Thomas E Denion
*Assistant Examiner* — Christopher Jetton
(74) *Attorney, Agent, or Firm* — Martin Fleit; Paul D. Bianco; Fleit Gibbons Gutman Bongini & Bianco PL

(57) ABSTRACT

The present invention discloses a self-regulating thermal energy storage system for use in conjunction with at least one thermal energy client, and a method for self-regulating the storage and use of thermal energy in the system.

18 Claims, 7 Drawing Sheets

SELF-REGULATED THERMAL ENERGY SYSTEM

CROSS REFERENCE TO RELATED APPLICATIONS

The present application is a Continuation-in-Part of and claims benefit of PCT International Application Serial No. PCT/IL2004/000360, entitled "THERMAL ENERGY STORAGE" filed on Apr. 29, 2004, which claims benefit of Israeli Patent Application Serial No. 155665, entitled "THERMAL ENERGY STORAGE" filed on Apr. 29, 2003, which are both incorporated herein by reference.

FIELD OF THE INVENTION

The present invention relates to self-regulated thermal energy systems.

BACKGROUND OF THE INVENTION

Various approaches have been taken in the art to generate thermal energy, wherein this energy is being either the presence of heat, as provided by a heating system, boiler, heat exchanger or the like, or the presence of cold, as provided by a cooling system, chiller, heat exchanger, or the like. In a simplified manner, a heat exchange system comprises two reciprocal steps: after a first thermal energy exchange, thermal energy carrier fluid is recycled from a thermal energy generator to a client, whereat a second (and opposite) thermal energy exchange is provided and vice versa.

More specifically, and as utilized in many industrial systems, the thermal energy is generated by one or more thermal energy generation sources and supplied in a predetermined capacity to at least one thermal energy client by a means of a conduit system, cycling at least one thermal energy carrier fluid, capable for effective and reversible supply of a predetermined measure of the thermal energy. In a simple case, the thermal requirements of the client are fixed and provided in a steady state along the day so that the thermal production capacity of the generator equals the thermal requirements of the client. In more complicated cases however, the thermal requirements of the client are not steady, e.g., the client's thermal requirements are temporarily lower than the generator's and solids tend to be distributed generally vertically, with warmer layers being positioned above cooler lower layers. A simple to operate and cost effective self-regulating thermal energy storage system is hence still a long felt need.

SUMMARY OF THE INVENTION

It is an aim of the present invention to provide a self-regulating thermal energy storage system (10) for use in conjunction with at least one thermal energy client (16), which comprising: (I) at least one thermal energy generation source (12) for imparting to at least one thermal energy carrier fluid a predetermined temperature change; (II) said at least one thermal energy client (16) is communicated in series, parallel or a combination thereof to said generator (12); (III) at least one thermal energy storage reservoir (14), adapted to store thermal energy generated by said generator (12) at the time that the said client (16) does not fully utilize said energy, communicated in parallel to a bypass of said storage and in series, parallel or a combination thereof to said generator (12) and said client (16); (IV) a first and a second fluid flow director, configured so that said first director (22A) is located at an upstream junction (USJ) in fluid communication with said generator (12), client (16) and reservoir (14); said first director (22A) functions to direct the flow of said fluid from the generator (12) in at least one of two directions, namely towards said client (16) and/or towards said reservoir (14); said second director (22B) is located at a downstream junction (DSJ) in fluid communication with said generator (12), client (16) and reservoir (14); said second director (22B) functions to direct the flow of said fluid towards the generator (12) in at least one of two directions, namely from said client (16) and/or from the reservoir (14). Said first and second fluid flow directors are interconnected with the DSJ-USJ supply line via $D_C$ or $D_H$, wherein $D_C$ or $D_H$ is a junction communicating said reservoir (14) and said DSJ-USJ supply line junction. When the thermal energy consumption of said client (16) equals the thermal energy generation capacity of said generator (12), said fluid is circulated directly from said generator (12) to said client (16) via said USJ, and vice versa, from said client (16) to said generator (12) via said DSJ; when the instantaneous thermal energy requirements of said client (16) are lower than the thermal energy generation capacity of said generator (12), only a portion of said fluid is circulated from said generator (12) to said client (16) via said USJ, and the remaining portion is diverted by said first director (22A) to said reservoir (14). In the case in which said generator (12) is adapted to cool said client (16) (a cooling system), a cold fluid is supplied to said lower portion of said reservoir (14) thereby causing a release of heat from the relatively warm layers of said storage medium in said upper portion thereof, while in the case in which said generator (12) is adapted to heat said client (16) (a heating system), a warm fluid is supplied to said higher portion of said reservoir (14) thereby causing a release of cold fluid from the relatively cold layers of said storage medium in said lower portion thereof. Fluids provided from said reservoir (14) and said client (16) are admixed in said DSJ, and supplied to said generator (12) by said second director (22B). In the specific case in which the instantaneous thermal energy requirements of said client (16) are approximately zero, said fluid is circulated directly from said generator (12) to said reservoir (14) via said USJ, preferably until the temperature of the outlet fluid at DSJ equals the temperature of the inlet fluid at said USJ.

More specifically, the aim of the present invention is to disclose the self-regulated thermal system (1) that is additionally comprises a first temperature sensor (12S) located upstream of said generator (12) and a second temperature sensor (16S) located downstream of said client (16). Said first sensor (12S) is in communication with said second director (22B) at the DSJ via a first processing means ($PLV_B$), and said second sensor (16S) is in communication with said first director (22A) at the USJ via a second processing means ($PLV_A$). Said processing means ($PLV_A$, $PLV_B$) are adapted to regulate said directors, such that when the thermal energy generating capacity of said generator (12) is lower than the thermal energy capacity (i.e., fluid temperature multiplied by fluid flux) of the fluid exiting said DSJ, said second director (22B) is adapted to supply more fluid than is directed from said reservoir (14), while when the instantaneous energy requirements of the thermal energy client (16) differ significantly from zero (namely, when the temperature of the fluid exiting said client (16) is different from a predetermined measure), said first director (22A) regulates the fluid exiting said USJ such that less fluid is supplied to said reservoir (14) and more fluid is supplied to said client (16), and vice versa.

It is therefore an object of the present invention to disclose a self-regulating thermal energy storage system (10) for use in conjunction with at least one thermal energy generation source (12) adapted to impart to at least one thermal energy carrier fluid a predetermined temperature change, at least one thermal energy storage reservoir (14), and at least one thermal energy client (16), wherein said thermal energy storage system comprises:

a. at least one mixing downstream junction (100), having a first entrance branch (101), a second entrance branch (102), and an exit branch (112);

b. at least one diverting upstream junction (200), having an entrance branch (212), a first exit branch (201), and a second exit branch (202), i. said entrance branch (212) in fluid connection with said exit branch (112) of said mixing downstream junction (100) through said at least one generator (12), said fluid connection (112-212) configured for one-way flow of said thermal energy carrier fluid from said exit branch (112) of said mixing downstream junction (100) through said at least one generator (12) to said entrance branch (212) of said diverting upstream junction (200);

ii. said first exit branch (201) in fluid connection with said first entrance branch (101) of said mixing downstream junction (100);

iii. said second exit branch (202) in fluid connection with said second entrance branch (102) of said mixing downstream junction (100) through said client (16), said fluid connection 202-102 in parallel to said fluid connection 201-101;

c. a junction $D_C$ in fluid connection with said first exit branch (201) of said diverting upstream junction (200) and said first entrance branch (101) of said mixing downstream junction (100), said junction $D_C$ located between said diverting upstream junction (200) and said mixing downstream junction (100);

d. a junction $E_C$ in fluid connection with said second exit branch (202) of said diverting upstream junction (200), said second entrance branch (102) of said mixing downstream junction (100), and said junction $D_C$, said fluid connection with said junction $D_C$ being through said reservoir (14) and configured to permit two-way flow of said thermal energy carrier fluid between $D_C$ and $E_C$ through said reservoir (14), said junction $E_C$ located between said client (16) and said mixing downstream junction (100); and, e. at least one first and at least one second fluid flow directors (22A and 22B) said first director (22A) located at said diverting upstream junction (200) and adapted to direct the flow of said fluid through said diverting upstream junction (200); said second director (22B) located at said mixing downstream junction (100) and adapted to direct the flow of said fluid through said mixing downstream junction (100); and further wherein said fluid flow directors control the flow of said thermal energy carrier fluid through said self-regulating thermal energy storage system such that the amount of thermal energy supplied to the client is substantially equal to the instantaneous thermal energy requirements of said client, substantially all thermal energy produced by said generator above said instantaneous thermal energy requirements of said client is transferred from said generator to said reservoir, and substantially all instantaneous thermal energy requirements of said client above the thermal energy generation capacity of said generator are transferred from said reservoir.

It is a further object of the present invention to disclose such a self-regulating thermal energy storage system (10), additionally comprising a first temperature sensor (12S) and a second temperature sensor (16S), wherein said first sensor (12S) is in thermal contact with a point located upstream of said diverting upstream junction. (200) and said client (16) and said second temperature sensor (16S) is in thermal contact with said client; and further wherein said first sensor (12S) is in communication with said second director (22B) at said mixing downstream junction (100) via a first processing means ($PLV_B$), and said second sensor (16S) is in communication with said first director (22A) at said diverting upstream junction (200) via a second processing means ($PLV_A$).

It is a further object of this invention to disclose a self-regulating thermal energy storage system (10) as defined in any of the above, wherein said at least one reservoir (14) is interconnected with said fluid connection 101-201 in a plurality of locations such that said thermal energy carrier fluid can enter said reservoir (14) into a layer chosen from the group consisting of a warm layer and a cold layer, and further wherein said reservoir (14) is interconnected with said fluid connection 102-202 in a plurality of locations such said thermal energy carrier fluid, can exit said reservoir from a layer chosen from the group consisting of a warm layer and a cold layer, whereby said self-regulating thermal energy storage system is adapted for both heating and cooling of at least one client (16).

It is a further object of this invention to disclose a self-regulating thermal energy storage system (10) as defined in any of the above, further comprising at least one pump in fluid connection with at least one of said at least one thermal energy generation source (12), said at least one reservoir (14), and said at least one client (16).

It is a further object of this invention to disclose a self-regulating thermal energy storage system (10) as defined in any of the above, comprising more than one thermal energy generation source (12) adapted to impart to at least one thermal energy carrier fluid a predetermined temperature change, wherein said thermal energy generation sources are interconnected in a manner chosen from the group consisting of series, parallel, and any combination thereof.

It is a further object of this invention to disclose such a self-regulating thermal energy storage system (10), wherein said thermal energy generation sources are of at least two different types.

It is a further object of this invention to disclose a self-regulating thermal energy storage system (10) as defined in any of the above, comprising more than one reservoir (14), wherein said reservoirs are interconnected in a manner chosen from the group consisting of series, parallel, and any combination thereof.

It is a further object of this invention to disclose such a self-regulating thermal energy storage system (10), wherein said reservoirs are of at least two different types.

It is a further object of this invention to disclose a self-regulating thermal energy storage system (10) as defined in any of the above, comprising more than one client (16), wherein said clients are interconnected in a manner chosen from the group consisting of series, parallel, and any combination thereof.

It is a further object of this invention to disclose such a self-regulating thermal energy storage system (10), wherein said clients are of at least two different types.

It is a further object of this invention to disclose a self-regulating thermal energy storage system (10) as defined in any of the above, comprising more than one mixing downstream junction, wherein said mixing downstream junctions are interconnected in a manner chosen from the group consisting of series, parallel, and any combination thereof.

It is a further object of this invention to disclose a self-regulating thermal energy storage system (10) as defined in any of the above, comprising more than one diverting upstream junction, wherein said diverting upstream junctions are interconnected in a manner chosen from the group consisting of series, parallel, and any combination thereof.

It is a further object of this invention to disclose a self-regulating thermal energy storage system (10) as defined in any of the above, wherein said at least one thermal energy generation source (12) comprises at least one solar collector.

It is a further object of this invention to disclose a self-regulating thermal energy storage system (10) as defined in any of the above, wherein said processing means ($PLV_A$, $PLV_B$) are adapted to regulate said directors, such that the amount of thermal energy supplied to said client is substantially equal to the instantaneous thermal energy requirements of said client, substantially all thermal energy produced by said generator above said instantaneous thermal energy requirements of said client is transferred from said generator to said reservoir, and substantially all instantaneous thermal energy requirements of said client above the thermal energy generation capacity of said generator are transferred from said reservoir.

It is a further object of this invention to disclose a self-regulating thermal energy storage system (10) as defined in any of the above, wherein said processing means ($PLV_A$, $PLV_B$) are adapted to regulate said directors, such that the mixing of said thermal energy carrier fluid at mixing downstream junction 100 yields thermal energy carrier fluid having a predetermined temperature as measured at a predetermined point within said system.

It is a further object of this invention to disclose such a self-regulating thermal energy storage system (10), wherein said predetermined point is the point measured by temperature sensor 12S.

It is a further object of this invention to disclose a method for self-regulating the storage and use of thermal energy in a thermal energy storage system (10) as defined in any of the above, adapted to determine the energy input requirements of said client (16) and the generation capacity of said thermal energy generation source (12), and at least one thermal energy carrier fluid susceptible to layering, said method comprising:
  a. opening said entrance branch 212 and said exit branch 112;
  b. generating energy in said thermal energy generation source (12) if said thermal energy generation source is operating;
  c. if said client (16) requires no energy input:
    i. closing said exit branch 202;
    ii. opening said exit branch 201, whereby at least part of said thermal energy carrier fluid enters said reservoir (14) via said junction $D_C$, thereby displacing energy carrier fluid that has not undergone any energy change in said thermal energy generation source from said reservoir (14) via junction $E_C$;
    iii. closing at least partially said entrance branch 101; and
    iv. opening at least partially said entrance branch 102 in tandem with said step of closing at least partially said entrance branch 101 such that thermal energy carrier fluid exits said mixing downstream junction via said exit branch 112 at a predetermined temperature;
  d. if the energy input requirement of said client (16) is less than the generation capacity of said thermal energy generation source (12):
    i. opening at least partially said exit branch 202 sufficiently that said thermal energy carrier fluid at a predetermined temperature flows to said client (16);
    ii. opening at least partially said exit branch 201, whereby at least part of said thermal energy carrier fluid enters said reservoir (14) via said junction $D_C$, thereby displacing energy carrier fluid that has not undergone any energy change in said thermal energy generation source from said reservoir (14) via junction $E_C$;
    iii. opening at least partially said entrance branch 102; and,
    iv. closing at least partially said entrance branch 101 in tandem with said step of opening at least partially said entrance branch 102 such that thermal energy carrier fluid exits said mixing downstream junction 100 via said exit branch 112 to a predetermined temperature;
  e. if the energy input requirement of said client (16) is equal to the generation capacity of said thermal energy generation source (12):
    i. opening said exit branch 202;
    ii. closing said exit branch 201;
    iii. opening said entrance branch 102; and,
    iv. closing said entrance branch 101;
  f. if the energy input requirement of said client (16) is greater than the generation capacity of said thermal energy generation source (12) and said thermal energy generation source (12) is in operation:
    i. opening said exit branch 202;
    ii. closing said exit branch 201, whereby at least part of said thermal energy carrier fluid enters said reservoir (14) via said junction $E_C$, thereby displacing energy carrier fluid that has not undergone any energy change in said thermal energy generation source from said reservoir (14) via junction $D_C$;
    iii. opening at least partially said entrance branch 101; and,
    iv. opening at least partially said entrance branch 102 in tandem with said step of opening at least partially said entrance branch, 101 sufficiently that thermal energy carrier fluid exiting said mixing downstream junction 100 via exit branch 112 is at a predetermined temperature; and,
  g. if said predetermined temperature change is zero:
    i. closing said entrance branch 102;
    ii. opening said entrance branch 101;
    iii. opening at least partially said exit branch 201; and,
    iv. opening at least partially said exit branch 202 in tandem with said step of opening at least partially said exit branch 201, whereby at least part of said thermal energy carrier fluid enters said reservoir (14) via said junction $E_C$, thereby displacing energy carrier fluid that has not undergone any energy change in said thermal energy generation source from said reservoir (14) via junction $D_C$, and such that the thermal energy carrier fluid flowing to said client (16) is provided according to the thermal energy requirements of said client (16).

It is a further object of this invention to disclose such a method, wherein said predetermined temperature of said thermal energy carrier fluid exiting said exit branch 112 is that temperature that will bring said thermal energy carrier fluid to a second predetermined temperature after passage through said thermal energy generation source (12).

BRIEF DESCRIPTION OF DRAWINGS

The present invention will be understood and appreciated more fully from the following detailed description taken in conjunction with the drawings in which.

DETAILED DESCRIPTION OF THE INVENTION

The following description is provided to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a self-regulating thermal energy storage system and a self-regulating method for use of such systems.

The term 'Energy generation source' or 'generator' refers hereinafter to any source of heat and/or cold. For example, it may be an electric or diesel powered boiler, a solar powered system, a geothermal system or the like; a chiller, or cold river or sea water or the like.

The term 'Energy client' or 'client' refers hereinafter to any 'beneficiary' of the stored energy to which energy (heat or cold) generated in the energy generation source is provided. The client can be a liquid, such as, freshly produced milk to be cooled, a solid, such as a molten iron to be cooled, or gas, such as air in an air cooling system. The client may receive the energy either directly or indirectly, for example, via a heat exchanger.

The term 'Energy reservoir' or 'reservoir' refers hereinafter to any body containing a thermal storage medium having a thermal heat capacity which may change phase or temperature. This medium stores either heat or cold energy by accumulation in thermal layers at a time when energy is generated and releases it to the client when it is required. This latter situation may arise when the energy required by the client at a particular moment is greater than the momentary energy production capacity of the energy generation source. The thermal storage medium may be a solid, such as, rock gravel, as used in domestic heat/cold reservoir systems, liquid, such as any suitable brine solution, or gas, such as steam, and so on. Most preferably, the thermal storage medium is a medium in which thermal layering occurs.

The term 'Conduit system' refers hereinafter to a conduit system that transfers energy from the energy generation source to the energy reservoir and/or to the energy client. It may include, as required, piping, ducts, valves, blowers, and pumps, and, generally, all hardware components that are required to facilitate energy transfer among the other system components. The conduit system may be open or closed, as will be appreciated from the detailed description herein.

The term 'Control system' refers hereinafter to any control equipment and software including thermostats, mechanized valve controllers, computer controls for pumps and blowers, etc.

Figure 1:
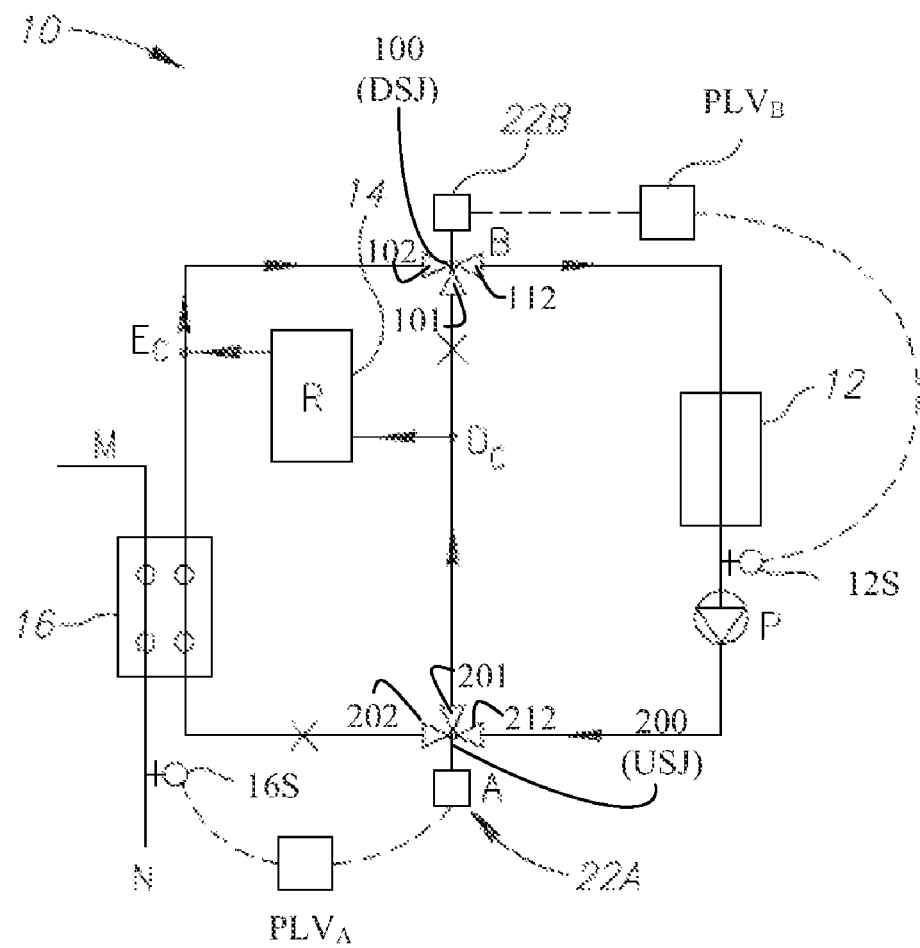
FIGS. 1 and 2 are schematic diagrams of a self-regulated thermal energy storage system (10) adapted for cooling (FIG. 1) and heating (FIG. 2) a client according to two embodiments of the present invention.

Reference is now made to FIG. 1, which presents a schematic diagram of a self-regulating thermal energy storage system (10) according to one embodiment of the present invention. System (10) is designed for use in conjunction with at least one thermal energy client (16). The system is especially useful for cooling, i.e., when the client requires a supply of cold, and comprises inter alia the following modules: At least one thermal energy generation source (12), useful for imparting to at least one thermal energy carrier fluid a predetermined temperature change. At least one thermal energy client (16) is communicated in series, parallel or a combination thereof to generator (12). At least one thermal energy storage reservoir (14) is adapted to store thermal energy generated by generator (12) at the time that the client (16) does not fully utilize the energy being generated. Reservoir (14) is connected in parallel to a bypass of said storage and in series, parallel or a combination thereof to generator (12) and client (16).

System (10) further comprises in a non-limiting manner first and second fluid flow directors. The directors are configured so that the first director (22A) is located at an upstream junction (USJ) that connects the generator (12), client (16) and reservoir (14). The first director (22A) functions to direct the flow of fluid from the generator (12) in at least one of two directions, namely towards client (16), towards reservoir (14), or towards both.

Second director (22B) is located at a downstream junction (DSJ) and connects generator (12), client (16) and reservoir (14). Second director (22B) functions to direct the flow of said fluid towards the generator (12) in at least one of two directions, namely from client (16) from the reservoir (14), of from both. Second director (22B) is interconnected with the DSJ-USJ supply line via $D_C$ in a cooling system, or via $D_H$ in a heating system, wherein $D_C$ and/or $D_H$ is a junction providing a connection between said reservoir (14) and the DSJ-USJ supply line.

In the simplest case, i.e. the thermal energy consumption of client (16) equals the thermal energy generation capacity of generator (12), the fluid is circulated directly from generator (12) to client (16) via the USJ, and vice versa, from said client (16) to generator (12) via the DSJ.

In the case in which the instantaneous thermal energy requirements of client (16) are lower than the thermal energy generation capacity of generator (12), only a portion of the fluid is circulated from said generator (12) to client (16) via the USJ, and the remaining portion is diverted by said first director (22A) towards reservoir (14).

In the case that generator (12) is adapted to cool client (16) (a cooling system, such as is depicted schematically in FIG. 1), a cold fluid is supplied to said lower portion of reservoir (14) thereby causing a release of heat from the relatively warm layers of said storage medium in said upper portion thereof.

Figure 2:
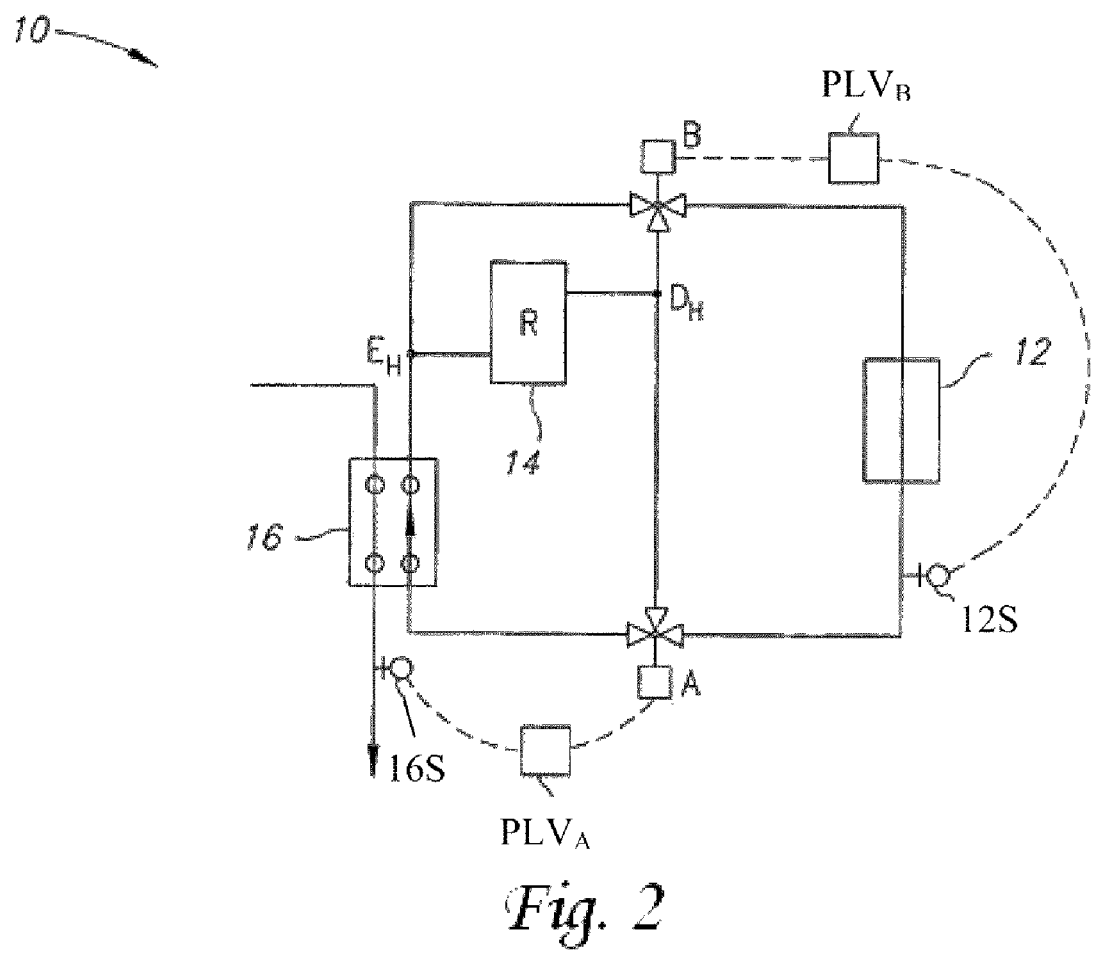

In the case that generator (12) is adapted to heat client (16) (a heating system, such as is depicted schematically in FIG. 2), a warm fluid is supplied to said upper portion of reservoir (14) thereby causing a release of cold fluid from the relatively cold layers of said storage medium in said lower portion thereof. Fluid provided from reservoir (14) and client (16) are admixed in said DSJ, and supplied to generator (12) by second director (22B).

In the case in which the instantaneous thermal energy requirement of the client (16) is approximately zero, the fluid is circulated directly from the generator (12) to the reservoir (14) via the USJ, preferably until the temperature of the outlet fluid at the DSJ equals the inlet fluid at the USJ.

System (10) as defined in any of the above may additionally comprise various sensors and hence provide for feed-backed regulation. For example and in a non-limiting manner, according to another embodiment of the present invention, a first temperature sensor (12S) and a second temperature sensor (16S) are provided. The first temperature sensor (12S) is located upstream of the USJ and client (16), and the second temperature sensor (16S) is in thermal contact with client (16); in the case in which there is a temperature gradient across client (16), the second temperature sensor is preferably in thermal contact with the low-temperature end of the gradient. The first sensor (12S) is in communication with the second director (22B) at the DSJ via a first processing means ($PLV_B$). The second sensor (16S) is in communication with the first director (22A) at the USJ via a second processing means ($PLV_A$).

The processing means ($PLV_A$, $PLV_B$) are adapted to regulate the aforesaid directors, such that when the thermal energy generating capacity of generator (12) is lower than the thermal energy capacity (i.e., fluid temperature multiplied by fluid flux) of the fluid exiting the DSJ, the second director (22B) supplies a greater portion of fluid directed from reservoir (14). Additionally or alternatively, when the instantaneous energy requirements of the thermal energy client (16), namely the temperature of the fluid exiting client (16), is different from a predetermined measure, the first director (22A) regulates the fluid output at USJ such that less fluid is supplied to reservoir (14) and more fluid is supplied to client (16), and vice versa.

According to one embodiment of the present invention, more than one generator is provided, the generators are preferably interconnected, either in series or in parallel. According to another embodiment of the present invention wherein more than one reservoir is provided; said reservoirs are preferably interconnected, either in series or in parallel. According to yet another embodiment of the present invention, more than one client is provided; said clients are preferably interconnected, either in series or in parallel.

According to another embodiment of the present invention, system (10) comprises more than one generator, said more than one generator being preferably adapted for both heating and cooling at least one client (16), wherein said reservoir is interconnected with said DSJ-USJ supply line in a plurality of locations such that said thermal energy carrier fluid can enter the reservoir through one of these locations into a warm layer (i.e. into the upper portion of the reservoir), or through a different location into a cold layer (i.e. into the lower portion of the reservoir), and further wherein said reservoir is interconnected with the line connecting said client and said DSJ in a plurality of locations such said thermal energy carrier fluid can exit said reservoir from a warm layer, or alternatively from cold layer, whereby said self-regulating thermal energy storage system is adapted for both heating and cooling of at least one client (16). Which point of entry and exit of the thermal energy carrier fluid into and out of the reservoir is used at any particular moment will depend on whether the system is being used to heat the client or to cool it.

The present invention also discloses a cost effective and novel method for self-regulating the storage and use of thermal energy in thermal energy storage system (10) as defined in any of the above. The method comprises inter alia steps of:

(i) selectably supplying heat to the upper portion of reservoir (14), thereby causing a release of cold from the relatively cold layers of the storage medium in the lower portion thereof; and (ii) selectably supplying cold to the lower portion of reservoir (14) thereby to causing a release of heat from the relatively warm layers of said storage medium in the upper portion thereof, in accordance with the instantaneous requirements of the thermal energy client (16) and the instantaneous generation capability of generation source (12).

The method described above may additionally comprise steps of:

(i) providing a plurality of fluid flow directors (22A, 22B) configured to assure that the volumetric flow of said thermal energy carrier fluid to the thermal energy client (16) and the thermal energy storage reservoir (14) is in accordance with the instantaneous energy requirements of the energy client (16) and the capability of the thermal energy generation source (12) to generate thermal energy;

(ii) locating said first director at an upstream junction (USJ) in connecting generator (12), client (16) and reservoir (14);

(iii) directing first director (22A) to direct the flow of the fluid from generator (12) in at least one of two directions, namely towards client (16), towards reservoir (14), or both;

(iv) locating the second director (22B) at a downstream junction (DSJ) connecting said generator (12), client (16) and reservoir (12);

(v) directing the second director (22B) (which is interconnected with the DSJ-USJ supply line) to direct the flow of the fluid towards generator (12) in at least one of two directions, namely from client (16), from reservoir (14), or both.

The method is especially useful when the thermal energy consumption of client (16) is equal to the thermal energy generation capacity of said generator (12). In this case, the method defines a step of circulating the fluid directly from generator (12) to client (16) via the USJ, and vice versa, from client (16) to generator (12) via the DSJ.

Alternatively, the method is especially useful wherein the instantaneous thermal energy requirements of client (16) are lower than the thermal energy generation capacity of generator (12). In this case, only a portion of said fluid from generator (12) is supplied to said client (16) via the USJ, and the remaining portion is diverted towards reservoir (14) by the first director (22A).

In the case that generator (12) is adapted to cool client (16) (a cooling system, FIG. 1), a step of supplying a cold fluid to the lower portion of reservoir (14) is provided, allowing release of heat from the relatively warm layers of the storage medium in the upper portion thereof.

In the case that generator (12) is adapted to heat said client (16) (a heating system, FIG. 2), the following steps are provided:

(i) supplying warm fluid to the higher portion of reservoir (14), allowing release of cold fluid from the relatively cold layers of the storage medium in the lower portion thereof;

(ii) admixing fluids provided from reservoir (14) and client (16) in the DSJ;

(iii) supplying the same to generator (12) by second director (22B).

In the case that the instantaneous thermal energy requirements of client (16) are approximately zero, a step of circulating the fluid directly from generator (12) to reservoir (14)

via the USJ is provided, preferably until the temperature of the outlet fluid at the DSJ equals that of the inlet fluid at the USJ.

According to yet another embodiment of the present invention, the first temperature is higher than the second temperature and the first extreme position is substantially near the top of said reservoir (14) and the second extreme position is substantially near the bottom of said reservoir (14).

According to yet another embodiment of the present invention, the first temperature is lower than the second temperature and the first extreme position is substantially near the bottom of said reservoir (14) and the second extreme position is substantially near the top of said reservoir (14).

Figure 3:
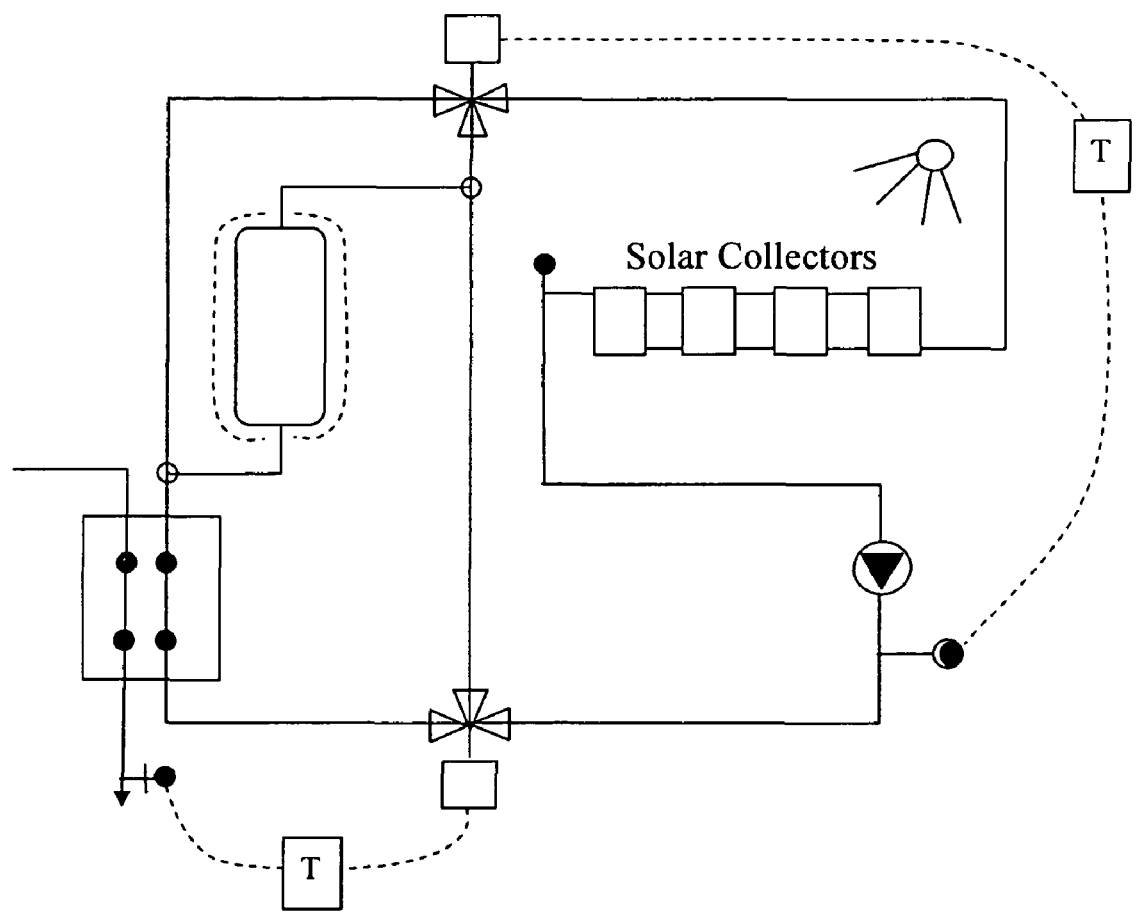
FIG. 3 is a schematic diagram of a self-regulated thermal energy storage system (10) adapted to heat a client by a set of solar collectors according to yet another embodiment of the present invention.

Reference is now made to FIG. 3, which shows schematically yet another embodiment of the present invention. In this embodiment of system (10), the "generator" is an array of one or more solar collectors interconnected in series, in parallel or in any combination thereof.

Figure 4:
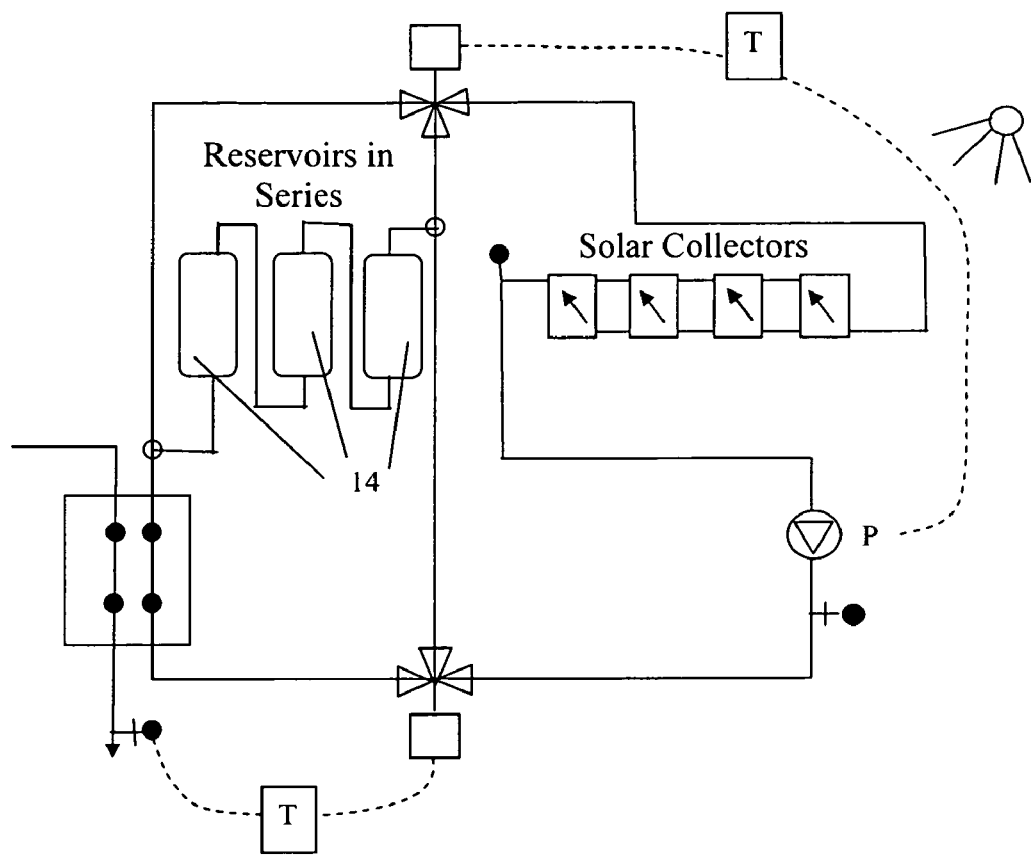
FIG. 4 is a schematic diagram of a self-regulated thermal energy storage system (10) adapted to heat a client by a set of solar collectors, with a set of reservoirs according to yet another embodiment of the present invention.

Reference is made now to FIG. 4, which shows schematically yet another embodiment of the present invention. This embodiment of system (10) includes a generator array (in the specific embodiment illustrated, a solar array as in FIG. 3) and a plurality of interconnected reservoirs. The reservoirs may be interconnected either in series, in parallel or in any combination thereof.

Figure 5:
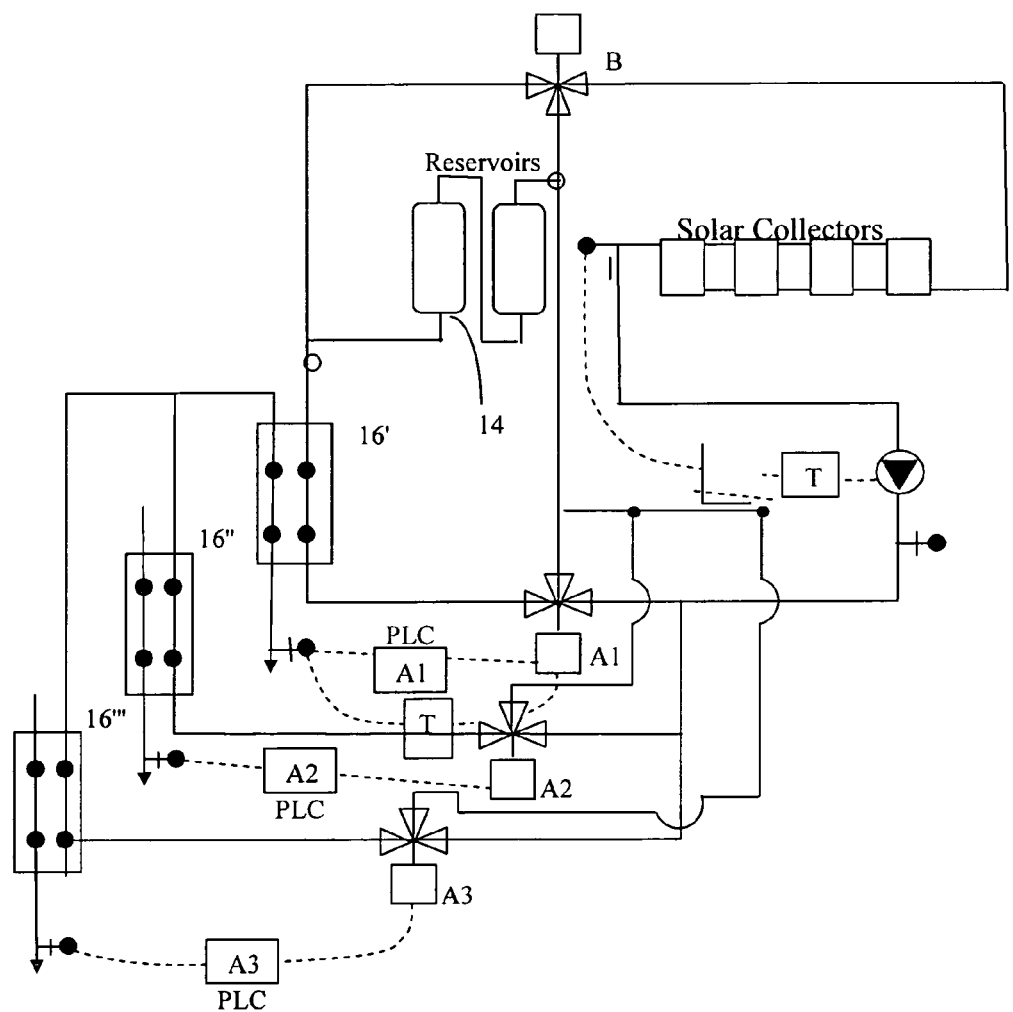
FIG. 5 is a schematic diagram of a self-regulated thermal energy storage system (10) adapted to heat a set of clients by a set of solar collectors according to yet another embodiment of the present invention.

Reference is made now to FIG. 5, which shows schematically yet another embodiment of the present invention. This embodiment of system (10) includes an array of generators (in the embodiment illustrated, the solar array of FIG. 3) and a plurality of interconnected reservoirs (in the embodiment illustrate, two reservoirs, as in FIG. 4), and a plurality (e.g., three) of clients. The generators, reservoirs, and clients may be interconnected either in series, in parallel or in any combination thereof.

Figure 6:
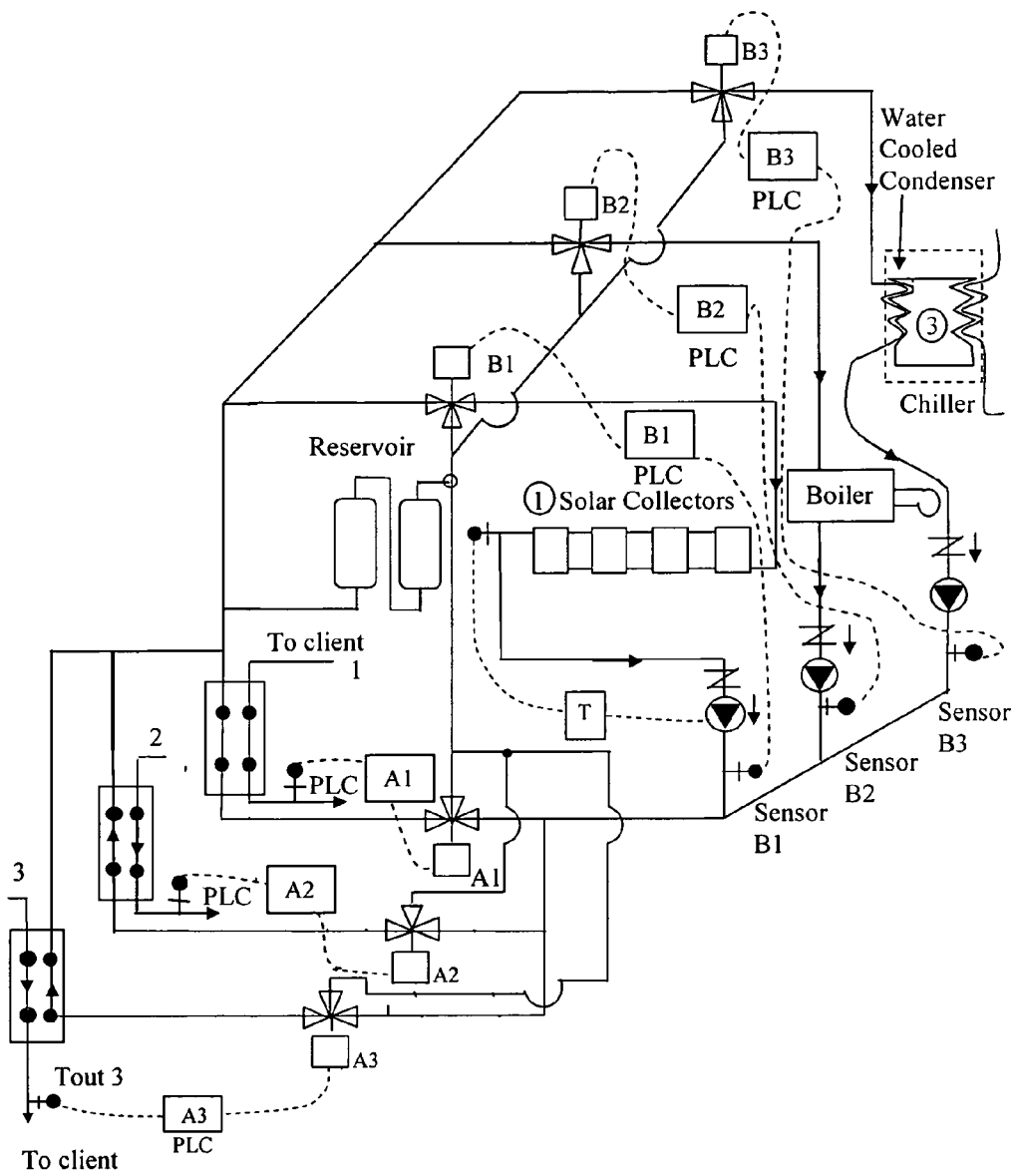
FIG. 6 is a schematic diagram of a self-regulated thermal energy storage system (10) adapted to heat and/or cool a set of clients by a various thermal generators according to yet another embodiment of the present invention; and, FIG. 7 is a schematic diagram of a self-regulated thermal energy storage system (10) adapted to heat a set of end users (e.g., domestic water systems) via one or more heat exchangers (client 16) by a thermal generator and a set of reservoirs according to yet another embodiment of the present invention.

Reference is made to FIG. 6, which shows schematically yet another embodiment of the present invention, comprising a plurality of interconnected self-regulated thermal energy systems (10). The systems may be interconnected in parallel, in series or in any combination thereof. In a preferred embodiment, the system is adapted for cooling and/or heating a plurality of clients, wherein the clients are interconnected in parallel, in series or in a combination thereof. This system is including an array of generators (in the specific embodiment illustrated, the solar array of FIG. 3), a boiler, a condenser, a chiller, etc. Also illustrated is a plurality of interconnected reservoirs, here, two reservoirs as illustrated in FIG. 4.

Figure 7:
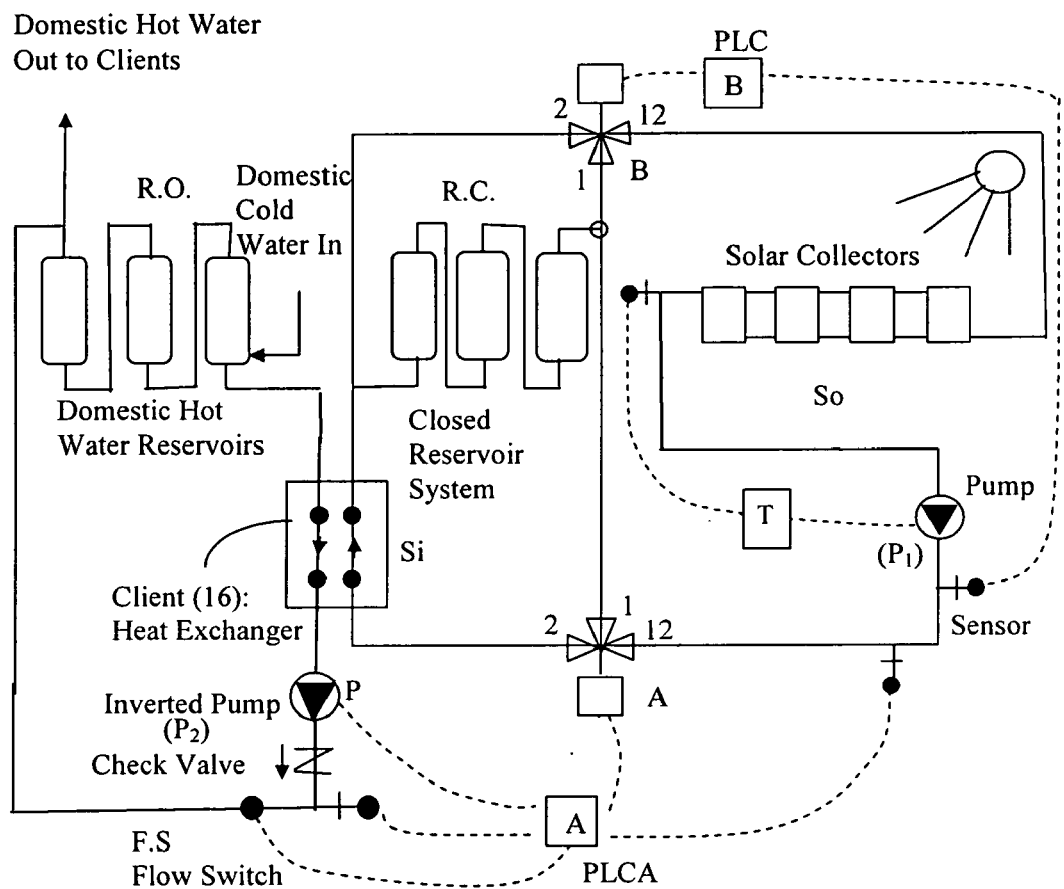
Figure 5:
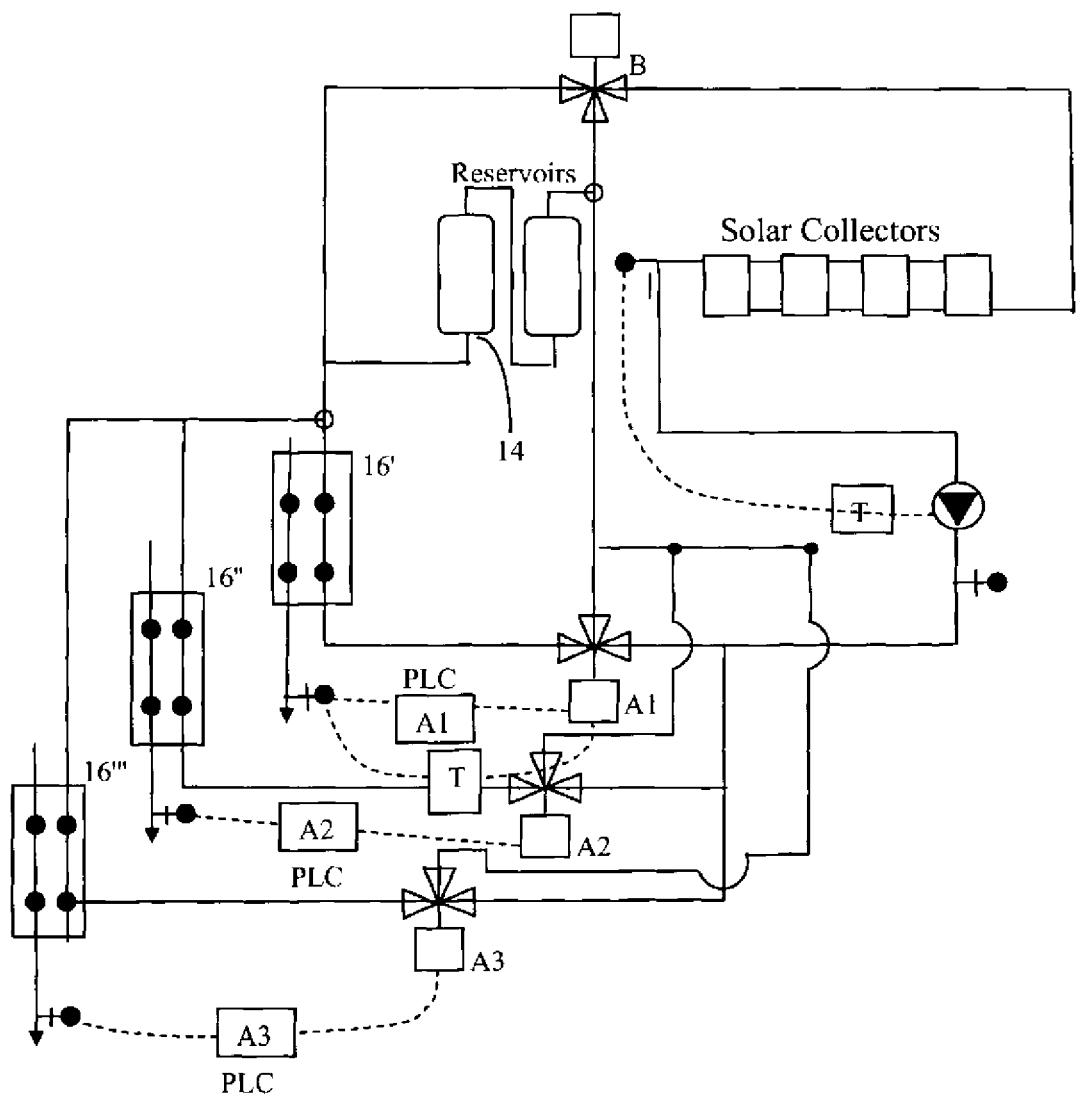

Reference is now made to FIG. 7, which shows schematically yet another embodiment of the present invention. In this embodiment, an array of four solar collectors generate heat, which is transferred to a central heat exchanger, which supplies heat to a plurality of end users, here domestic clients for either hot and cold water. A cascade of three reservoirs is used.

It will be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A self-regulating thermal energy storage system (10) for use in conjunction with at least one thermal energy generation source (12) adapted to impart to at least one thermal energy carrier fluid a predetermined temperature change, at least one thermal energy storage reservoir (14), and at least one thermal energy client (16), wherein said thermal energy storage system comprises:

a. at least one mixing downstream junction (100), having a first entrance branch (101), a second entrance branch (102), and an exit branch (112);
 b. at least one diverting upstream junction (200), having an entrance branch (212), a first exit branch (201), and a second exit branch (202),
   i. said entrance branch (212) in fluid connection with said exit branch (112) of said mixing downstream junction (100) through said at least one generator (12), said fluid connection (112-212) configured for one-way flow of said thermal energy carrier fluid from said exit branch (112) of said mixing downstream junction (100) through said at least one generator (12) to said entrance branch (212) of said diverting upstream junction (200);
   ii. said first exit branch (201) in fluid connection with said first entrance branch (101) of said mixing downstream junction (100);
   iii. said second exit branch (202) in fluid connection with said second entrance branch (102) of said mixing downstream junction (100) through said client (16), said fluid connection 202-102 in parallel to said fluid connection 201-101;
 c. a junction $D_C$ in fluid connection with said first exit branch (201) of said diverting upstream junction (200) and said first entrance branch (101) of said mixing downstream junction (100), said junction $D_C$ located between said diverting upstream junction (200) and said mixing downstream junction (100);
 d. a junction $E_C$ in fluid connection with said second exit branch (202) of said diverting upstream junction (200), said second entrance branch (102) of said mixing downstream junction (100), and said junction $D_C$, said fluid connection with said junction $D_C$ being through said reservoir (14) and configured to permit two-way flow of said thermal energy carrier fluid between $D_C$ and $E_C$ through said reservoir (14), said junction $E_C$ located between said client (16) and said mixing downstream junction (100); and,
 e. at least one first and at least one second fluid flow directors (22A and 22B), said first director (22A) located at said diverting upstream junction (200) and adapted to direct the flow of said fluid through said diverting upstream junction (200); said second director (22B) located at said mixing downstream junction (100) and adapted to direct the flow of said fluid through said mixing downstream junction (100);

and further wherein said fluid flow directors control the flow of said thermal energy carrier fluid through said self-regulating thermal energy storage system such that the amount of thermal energy supplied to the client is substantially equal to the instantaneous thermal energy requirements of said client, substantially all thermal energy produced by said generator above said instantaneous thermal energy requirements of said client is transferred from said generator to said reservoir, and substantially all instantaneous thermal energy requirements of said client above the thermal energy generation capacity of said generator are transferred from said reservoir.

2. A self-regulating thermal energy storage system (10) according to claim 1, additionally comprising a first temperature sensor (12S) and a second temperature sensor (16S), wherein said first sensor (12S) is in thermal contact with a point located upstream of said diverting upstream junction (200) and said client (16) and said second temperature sensor (16S) is in thermal contact with said client; and further wherein said first sensor (12S) is in communication with said second director (22B) at said mixing downstream junction (100) via a first processing means (PLV$_B$), and said second sensor (16S) is in communication with said first director (22A) at said diverting upstream junction (200) via a second processing means (PLV$_A$).

3. A self-regulating thermal energy storage system (10) according to claim 1, wherein said at least one reservoir (14) is interconnected with said fluid connection 101-201 in a plurality of locations such that said thermal energy carrier fluid can enter said reservoir (14) into a layer chosen from the group consisting of a warm layer and a cold layer, and further wherein said reservoir (14) is interconnected with said fluid connection 102-202 in a plurality of locations such said thermal energy carrier fluid can exit said reservoir from a layer chosen from the group consisting of a warm layer and a cold layer, whereby said self-regulating thermal energy storage system is adapted for both heating and cooling of at least one client (16).

4. A self-regulating thermal energy storage system (10) according to claim 1, further comprising at least one pump in fluid connection with at least one of said at least one thermal energy generation source (12), said at least one reservoir (14), and said at least one client (16).

5. A self-regulating thermal energy storage system (10) according to claim 1, comprising more than one thermal energy generation source (12) adapted to impart to at least one thermal energy carrier fluid a predetermined temperature change, wherein said thermal energy generation sources are interconnected in a manner chosen from the group consisting of series, parallel, and any combination thereof.

6. A self-regulating thermal energy storage system (10) according to claim 5, wherein said thermal energy generation sources are of at least two different types.

7. A self-regulating thermal energy storage system (10) according to claim 1, comprising more than one reservoir (14), wherein said reservoirs are interconnected in a manner chosen from the group consisting of series, parallel, and any combination thereof.

8. A self-regulating thermal energy storage system (10) according to claim 7, wherein said reservoirs are of at least two different types.

9. A self-regulating thermal energy storage system (10) according to claim 1, comprising more than one client (16), wherein said clients are interconnected in a manner chosen from the group consisting of series, parallel, and any combination thereof.

10. A self-regulating thermal energy storage system (10) according to claim 9, wherein said clients are of at least two different types.

11. A self-regulating thermal energy storage system (10) according to claim 1, comprising more than one mixing downstream junction, wherein said mixing downstream junctions are interconnected in a manner chosen from the group consisting of series, parallel, and any combination thereof.

12. A self-regulating thermal energy storage system (10) according to claim 1, comprising more than one diverting upstream junction, wherein said diverting upstream junctions are interconnected in a manner chosen from the group consisting of series, parallel, and any combination thereof.

13. A self-regulating thermal energy storage system (10) according to claim 1, wherein said at least one thermal energy generation source (12) comprises at least one solar collector.

14. A self-regulating thermal energy storage system (10) according to claim 2, wherein said processing means (PLV$_A$, PLV$_B$) are adapted to regulate said directors, such that the amount of thermal energy supplied to said client is substantially equal to the instantaneous thermal energy requirements of said client, substantially all thermal energy produced by said generator above said instantaneous thermal energy requirements of said client is transferred from said generator to said reservoir, and substantially all instantaneous thermal energy requirements of said client above the thermal energy generation capacity of said generator are transferred from said reservoir.

15. A self-regulating thermal energy storage system (10) according to claim 2, wherein said processing means (PLV$_A$, PLV$_B$) are adapted to regulate said directors, such that the mixing of said thermal energy carrier fluid at mixing downstream junction 100 yields thermal energy carrier fluid having a predetermined temperature as measured at a predetermined point within said system.

16. A self-regulating thermal energy storage system (10) according to claim 15, wherein said predetermined point is the point measured by temperature sensor 12S.

17. A method for self-regulating the storage and use of thermal energy in a thermal energy storage system (10) according to claim 1, adapted to determine the energy input requirements of said client (16) and the generation capacity of said thermal energy generation source (12), and at least one thermal energy carrier fluid susceptible to layering, said method comprising;
   a. opening said entrance branch 212 and said exit branch 112;
   b. generating energy in said thermal energy generation source (12) if said predetermined temperature change is not equal to zero;
   c. if said client (16) requires no energy input:
     i. closing said exit branch 202;
     ii. opening said exit branch 201, whereby at least part of said thermal energy carrier fluid enters said reservoir (14) via said junction D$_C$, thereby displacing energy carrier fluid that has not undergone any energy change in said thermal energy generation source from said reservoir (14) via, unction E$_C$;
     iii. closing at least partially said entrance branch 101; and,
     iv. opening at least partially said entrance branch 102 in tandem with said step of closing at least partially said entrance branch 101 such that thermal energy carrier fluid exits said mixing downstream junction via said exit branch 112 at a predetermined temperature;
   d. if the energy input requirement of said client (16) is less than the generation capacity of said thermal energy generation source (12):
     i. opening at least partially said exit branch 202 sufficiently that said thermal energy carrier fluid at a predetermined temperature flows to said client (16);
     ii. opening at least partially said exit branch 201, whereby at least part of said thermal energy carrier fluid enters said reservoir (14) via said junction D$_C$, thereby displacing energy carrier fluid that has not undergone any energy change in said thermal energy generation source from said reservoir (14) via junction E$_C$;
     iii. opening at least partially said entrance branch 102; and,
     iv. closing at least partially said entrance branch 101 in tandem with said step of opening at least partially said entrance branch 102 such that thermal energy carrier fluid exits said mixing downstream junction 100 via said exit branch 112 to a predetermined temperature;
   e. if the energy input requirement of said client (16) is equal to the generation capacity of said thermal energy generation source (12):
     i. opening said exit branch 202;

ii. closing said exit branch 201;
iii. opening said entrance branch 102; and,
iv. closing said entrance branch 101;

f. if the energy input requirement of said client (16) is greater than the generation capacity of said thermal energy generation source (12) and said thermal energy generation source (12) is in operation:
  i. opening said exit branch 202;
  ii. closing said exit branch 201, whereby at least part of said thermal energy carrier fluid enters said reservoir (14) via said junction $E_C$, thereby displacing energy carrier fluid that has not undergone any energy change in said thermal energy generation source from said reservoir (14) via junction $D_C$;
  iii. opening at least partially said entrance branch 101; and,
  iv. opening at least partially said entrance branch 102 in tandem with said step of opening at least partially said entrance branch 101 sufficiently that thermal energy carrier fluid exiting said mixing downstream junction 100 via exit branch 112 is at a predetermined temperature; and, g. if said predetermined temperature change is zero:
  i. closing said entrance branch 102;
  ii. opening said entrance branch 101;
  iii. opening at least partially said exit branch 201; and,
  iv. opening at least partially said exit branch 202 in tandem with said step of opening at least partially said exit branch 201, whereby at least part of said thermal energy carrier fluid enters said reservoir (14) via said junction $E_C$, thereby displacing energy carrier fluid that has not undergone any energy change in said thermal energy generation source from said reservoir (14) via junction $D_C$, and such that the thermal energy carrier fluid flowing to said client (16) is provided according to the thermal energy requirements of said client (16).

18. The method according to claim 17, wherein said predetermined temperature of said thermal energy carrier fluid exiting said exit branch 112 is that temperature that will bring said thermal energy carrier fluid to a second predetermined temperature after passage through said thermal energy generation source (12).

* * * * *

UNITED STATES PATENT AND TRADEMARK OFFICE
CERTIFICATE OF CORRECTION

| | |
|---|---|
| PATENT NO. | : 7,997,079 B2 |
| APPLICATION NO. | : 11/510876 |
| DATED | : August 16, 2011 |
| INVENTOR(S) | : Seidel |

It is certified that error appears in the above-identified patent and that said Letters Patent is hereby corrected as shown below:

In The Drawings:

Delete fig. 5 and substitute therefor the drawing sheet, consisting of fig. 5 as shown on the attached page.

Signed and Sealed this
Second Day of July, 2013

Teresa Stanek Rea
*Acting Director of the United States Patent and Trademark Office*